United States Patent [19]

Hirose et al.

[11] Patent Number: 5,104,996
[45] Date of Patent: Apr. 14, 1992

[54] PROCESS FOR PREPARING 2,3,5-TRIMETHYLBENZOQUINONE

[75] Inventors: Noriyasu Hirose, Kokubunji; Kimio Hamamura, Kashiwa; Yuichi Inai, Tokyo; Kiiti Ema, Tokyo; Takashi Banba, Tokyo; Shizumasa Kijima, Kashiwa, all of Japan

[73] Assignee: Eisai Co., Ltd., Tokyo, Japan

[21] Appl. No.: 192,661

[22] Filed: May 11, 1988

[30] Foreign Application Priority Data

May 13, 1987 [JP] Japan ................................. 62-116665

[51] Int. Cl.$^5$ ........................ C07C 46/08; C07C 50/04
[52] U.S. Cl. .................................................... 552/310
[58] Field of Search ..................... 260/396 R; 552/310

[56] References Cited

U.S. PATENT DOCUMENTS 3,663,578  3/1972  Kutepow et al. ............... 260/396 R
3,796,732  3/1974  Brenner ........................... 260/396 R

OTHER PUBLICATIONS

Perry et al., Techniques of Chemistry, vol. XII Separation and Purification, 3rd. Ed., John Wiley & Sons, N.Y. pp. 51–55, 1980.

Primary Examiner—Vivian Garner
Attorney, Agent, or Firm—Birch, Stewart, Kolasch & Birch

[57] ABSTRACT

2,3,5-trimethyl-benzoquinone is produced by oxidizing 2,3,6-trimethyl-phenol in the presence of a catalyst of cupric chloride and lithium chloride in a solvent mixture of an aromatic hydrocarbon and a lower aliphatic alcohol having 1 to 4 carbon atoms.

8 Claims, No Drawings

PROCESS FOR PREPARING 2,3,5-TRIMETHYLBENZOQUINONE

This invention relates to a process for preparing 2,3,5-trimethylbenzoquinone useful as an intermediate for synthesizing pharmaceuticals such as vitamin E.

BACKGROUND OF THE INVENTION

There are various known processes for preparing benzoquinone which comprise oxidizing a phenol compound with oxygen in the presence of a metallic ion catalyst, such as Cu, Mn, or Co. They include, for example, those described in the specifications, of Japanese Patent Publication Nos. 17585/1978, 52889/1981, and 37255/1986, Japanese Patent Laid-Open Nos. 12334/1979 and 48726/1979, and U.S. Pat. No. 4,257,968, 4,360,469, and 4442036.

Among them, e.g., Japanese Patent Laid-Open No. 48726/1979 discloses a process which is relatively suitable for practical use, i.e., a process for preparing benzoquinone which comprises oxidizing phenol with oxygen in the presence of cupric chloride and lithium chloride.

However, this process is not very suited for practical use because of the difficulty in recovering the catalyst and the necessity of conducting the oxidation under pressure in an autoclave.

Further, there are disclosed various processes for preparing 2,3,5-trimethylbenzoquinone (hereinafter abbreviated to "TMQ") which comprise oxidizing 2,3,6-trimethylphenol (hereinafter abbreviated to "TMP"). These include, for example, those described in the specifications of Japanese Patent Publication No. 17585/1978 and Japanese Patent Laid-Open Nos. 93931/1975, 36641/1974, 92033/1974, 126636/1974, 14641/1975, and 72136/1980. However, these processes also have various drawbacks. For example, the catalysts used in these processes exhibit only a low catalytic activity in an aqueous solution. Further, because of the use of an organic solvent which is easily soluble in water, the catalyst must be dissolved in water in recovering the product, which makes it very difficult to recover the catalyst from the resulting aqueous solution.

Further, Japanese Patent Laid-Open Nos. 225137/1984, 81135/1985, 255745/1985, 255746/1985, and 17532/1986 each disclose a process in which the oxidation is conducted with a copper-halogeno complex (e.g., $LiCuCl_3$, $KCuCl_3$, or $NH_4CHCl_3$) in the presence of an alkali metal halide. However, this process as well has drawbacks, e.g., that the preparation of a catalyst, i.e., a copper-halogeno complex crystal, is troublesome and that the use of a high-boiling higher aliphatic alcohol as the solvent in the reaction makes this process very disadvantageous with respect to the removal of the solvent at the time of isolating TMQ from an extract after the reaction, which renders this process commercially unsuitable.

The present inventors have made extensive and intensive studies with a view to developing a process which can eliminate the drawbacks of the above-detailed prior art and is more advantageous from the commercial viewpoint. Specifically, the present inventors have made studies for many years on a process which meets the three following requirements: ① use of a catalyst comprising a combination of commercially available common reagents rather than the use of an expensive special catalyst; ② use of a catalyst which exhibits a high catalytic activity, undergoes no deterioration of the catalytic activity and can be repeatedly used; and ③ use of a solvent system for reaction which enables not only the formation of a product in a high yield but also facilitates the isolation and purification of the product.

SUMMARY OF THE INVENTION

As a result, the present inventors have found that the desired objects can be attained by the following process.

Thus the present invention provides a process for preparing 2,3,5-trimethylbenzoquinone which comprises oxidizing 2,3,6-trimethylphenol in the presence of a catalyst composed of cupric chloride and lithium chloride, characterized in that a mixture of an aromatic hydrocarbon with a lower aliphatic alcohol having 1 to 4 carbon atoms is used as a solvent.

In the invention 2,3,5-trimethyl-benzoquinone is produced by the step of oxidizing 2,3,6-trimethyl-phenol in the presence of a catalyst of cupric chloride and lithium chloride in a solvent mixture of an aromatic hydrocarbon and a lower aliphatic alcohol having 1 to 4 carbon atoms.

It is preferable that the solvent mixture comprises the aromatic hydrocarbon and the lower aliphatic alcohol at a volume ratio of 1 : 0.2 to 1.

A preferable embodiment of the invention process comprises the steps of agitating the organic phase comprising 2,3,6-trimethyl-phenol and the solvent mixture and the aqueous phase comprising the catalyst and water to get a fine dispersion, bringing the dispersion with molecular oxygen or a molecular oxygencontaining gas to effect the oxidation of the 2,3 6-trimethyl-phenol and separating the organic phase containing the product from the aqueous phase. The above defined process is practically followed by the step of recovering the solvents by distillation of the organic phase and separating the aqueous phase for re-use thereof.

More specifically, the present invention provides a process for preparing TMQ which comprises bringing TMP into contact with molecular oxygen or a molecular oxygen-containing gas in an aqueous solution of a catalyst composed of cupric chloride, which is an inexpensive commercially available common reagent, in the presence of lithium chloride, characterized in that a mixture which is both hydrophilic and lipophilic and comprising an aromatic hydrocarbon and a lower aliphatic alcohol having 1 to 4 carbon atoms is added to the aqueous catalyst solution, thereby smoothly oxidizing TMQ.

The catalyst used in the present invention is a mixture of cupric chloride with lithium chloride and generally used in the form of an aqueous solution.

With respect to the composition ratio of the catalyst mixture comprising cupric chloride and lithium chloride, there is a tendency for the catalytic effect to increase with an increase in the amount of lithium chloride used per mol of cupric chloride. In fact, lithium chloride is generally used in an amount of 1 to 5 times by mole of cupric chloride. It is particularly preferred that lithium chloride be used in an amount of about 4 times by mole of cupric chloride, i.e., in an amount equal to that of cupric chloride by weight.

With respect to the concentration of the aqueous solution of the catalytic system comprising cupric chloride and lithium chloride, a higher concentration gives a better result with respect to the efficiency of the oxidation. However, the concentration is preferably 30 to 50%, particularly preferably 40% from the standpoint of the solubility of the catalyst in water and the agitation efficiency.

The oxidation can be conducted by commonly accepted methods. Representative examples of the methods include one in which molecular oxygen is used and one in which a molecular oxygen-containing gas, such as pure oxygen, oxygen-enriched air, or air, is used.

Although the above-described oxygen source gas may be bubbled into the reaction mixture under atmospheric pressure or higher pressure, the bubbling under atmospheric pressure is advantageous from the operation and economical viewpoints.

The bubbling rate varies depending upon reaction conditions, such as the shape of the reaction vessel, the agitation efficiency, the scale of the reaction, the reaction temperature, and the kind and bubbling method with respect to the oxygen source gas used, and therefore cannot be numerically expressed. However, the oxygen source gas should be supplied in an amount exceeding that of oxygen consumed in the oxidation of TMP, and the amount of supply can be determined experimentally.

In a reaction system in which pure oxygen is used, in order to increase the yield of TMQ and, at the same time, to improve the economy of the amount of oxygen used, it is preferred that the amount of supplied oxygen and the amount of exhausted oxygen be continuously measured and that the flow rate of the oxygen source gas be adjusted based on the obtained data so that 5 to 10% of the oxygen supplied is always exhausted.

Further, it is possible to allow the oxidation to efficiently proceed under a constant pressure by a gas circulation method while making up for the consumed oxygen.

The characteristic feature of the present invention resides in the use of a mixture of an aromatic hydrocarbon with a lower aliphatic alcohol having 1 to 4 carbon atoms as a solvent in a process for preparing 2,3,5-trimethylbenzoquinone which comprises oxidizing 2,3,6-trimethylphenol in the presence of a catalyst composed of cupric chloride and lithium chloride. The present inventors have found a surprising effect attained by this feature. The solvent used in the reaction will now be described in more detail.

The aromatic hydrocarbon is preferably one having a relatively low boiling point and excellent stability against oxidation, such as benzene, toluene, xylene, or chlorobenzene. Examples of the lower aliphatic alcohol having 1 to 4 carbon atoms include methanol, ethanol, n-propanol, isopropanol, n-butanol, 2-butanol, and tert-butanol.

In the present invention, at least one of the above-described aromatic hydrocarbons is combined with at least one of the above-described lower aliphatic alcohols for use in the form of a mixture. The most preferred combination among the above possible combinations is that of toluene with n-propanol and that of benzene with ethanol.

The composition ratio varies depending upon the combination of the aromatic hydrocarbon with the lower aliphatic alcohol and, therefore, cannot simply be determined. However, the volume ratio of the aliphatic lower alcohol to the aromatic hydrocarbon is preferably 0.2 to 1, particularly preferably 0.25 to 0.5.

When the oxidation according to the present invention is conducted in a solvent comprising only the above-described lower aliphatic alcohol, TMQ is formed as can be seen from the comparative examples which will be described later. However, in this case, the production of TMQ in a high yield could not be attained because of the formation of a large amount of by-products which appear to be hexamethylbiphenol and polymers. Further, in the post-treatment as well, this method has a drawback that the reaction mixture should be poured into a large amount of water, and thereafter the extraction with an organic solvent should be conducted. Moreover, with respect to the recovery of the catalyst, it is practically impossible to recover cupric chloride and lithium chloride from the diluted aqueous solution. The discard of the aqueous solution unfavorably causes a serious pollution problem.

On the other hand, when the oxidation was conducted in a solvent comprising only the aromatic hydrocarbon, an organic phase containing TMP dissolved therein and a water phase containing the catalyst mixture remained separated from each other even under vigorous agitation as can be seen from the comparative examples which will be described later. Therefore, the efficiency of contact among the organic phase, water phase, and the gaseous phase was remarkably low, and substantially no oxidation proceeded. As a result, the recovered substance substantially consisted of only the starting material.

The use of a solvent mixture comprising the aromatic hydrocarbon and the lower aliphatic alcohol in a suitably adjusted proportion revealed that the organic phase containing TMP dissolved therein and the water phase containing the catalyst were finely dispersed in each other during agitation to substantially form a suspension, which contributed to a marked improvement in the efficiency of contact among TMP, the catalyst, and molecular oxygen and a smooth progression in the oxidation, resulting in the formation of TMQ in a remarkably high yield. This surprising fact is thought to be brought about because the lipophilic nature of the aromatic hydrocarbon and the hydrophilic nature of the lower aliphatic alcohol are exhibited in a mixture comprising both components in a suitable proportion. The mixture functions as a solvent for the reaction having a combination of both hydrophilic and lipophilic natures, which enhances the efficiency of contact among the organic phase, the water phase, and the gaseous phase.

Another advantage of the present process is that in the solvent system used in the present invention, the reaction mixture is quickly and completely separated into an organic phase and a water phase as soon as the agitation and the supply of the gas are stopped after the completion of the reaction. Therefore, the catalyst phase, i.e., the water phase, and the organic phase containing TMQ dissolved therein can easily be separated from each other, which makes it very easy to repeatedly use the aqueous catalyst solution and to treat the organic solvent phase for collecting the formed TMQ.

Further, the aromatic hydrocarbon and the lower aliphatic alcohol used in the present invention (e.g., toluene and n-propanol) have each a boiling point lower than that of long-chain aliphatic alcohols (e.g., n-hexanol or n-octanol), which leads to an advantage with respect to the removal of these compounds. In addition, since the organic solvent suffers no significant loss during the recovery thereof by virtue of the salting-out effect of the concentrated aqueous catalyst solution, the organic solvent can be re-used with supply of a small amount of a fresh organic solvent compensating for the amount of loss. Further, the recovered aqueous catalyst solution is substantially free from the organic phase and, therefore, can be re-used in itself as the aqueous catalyst solution without any treatment. Thus, the present process has various economical advantages. The present invention has been completed based on the above-described surprising effects.

Although the reaction temperature in the present invention varies depending upon the composition of the solvent used, generally the reaction temperature is preferably 40° to 80° C., particularly preferably about 60° C. from the standpoint of the reaction rate and the suppression of the formation of by-products. The oxidation conducted on a large scale causes a rise in the reaction temperature due to the heat buildup. In such a case, the heat can easily be removed by adjusting the feed rate of TMP and reducing the feed rate of oxygen to suppress the progress of the reaction, thus enabling the control of the reaction temperature.

In the present invention, a substantially satisfactory yield of TMQ can be attained even when TMP is fed by a method which comprises preliminarily adding the total amount of TMP to a mixture of the aqueous catalyst solution with the solvent for reaction prior to the initiation of the reaction and conducting the oxidation through molecular oxygen. However, with respect to the feed of TMP to the reaction system, it is preferred from the standpoint of the suppression of the formation of by-products that TMP be gradually added in a rate equal to or slightly slower than the oxidation rate. Although the feed rate of TMP cannot simply be determined because it varies depending upon various factors such as the scale of the reaction, the amount of the catalyst used, the agitation efficiency, the kind and flow rate of the oxygen source gas used, and the reaction temperature, it is preferred that TMP be fed as slowly as possible However, in order to avoid prolongation of the reaction time, when the scale of the reaction is medium or larger, the other reaction conditions are adjusted so that the feed of TMP is completed generally after 2 to 7 hr, preferably 3 to 4 hr. In this connection, it is necessary for the reaction to be continued for an additional 1 to 3 hr after the completion of the addition of TMP for the purpose of completely oxidizing the remaining starting material and intermediates.

The reaction in the present invention is basically the so-called three-phase reaction which is conducted by bubbling an oxygen-base gas into a two-liquid system, i.e., TMP dissolved in an organic phase comprising an aromatic hydrocarbon and a lower aliphatic alcohol and having a combination of suitable hydrophilic and lipophilic natures and a catalyst dissolved in a water phase. For this reason, the reaction vessel should be provided with efficient agitating and bubbling devices. The provision of these devices enables efficient contact among the organic phase, the water phase, and the gaseous.

According to the present invention, TMP can be converted into TMQ in a very high yield by bubbling molecular oxygen or a molecular oxygen-containing gas under a mild conditions in a solvent comprising an aromatic hydrocarbon and a lower aliphatic alcohol in a suitable proportion in the presence of a catalyst composed of cupric chloride and lithium chloride which are commercially available inexpensive common reagents.

Further, according to the present invention, the product, i.e., TMQ, can easily be isolated and purified. Specifically, since the solvent system comprising an aromatic hydrocarbon and a lower aliphatic alcohol in a suitable proportion has a combination of hydrophilic and lipophilic natures, the solvent system and the catalyst in the water phase form an excellent suspension under agitation during oxidation, which brings about smooth progress the reaction among the three phases, i.e., the water phase, the organic phase, and the gaseous phase. As soon as the agitation is stopped after the completion of the reaction, the organic phase and the water phase are rapidly separated from each other, which leads to an advantage with respect to subsequent procedures.

Specifically, TMQ can easily be obtained by the withdrawal of the organic phase followed by the removal of the solvent by distillation, while the catalyst layer, i.e., the water phase, is substantially free from the organic phase by virtue of the salting-out effect and, therefore, can advantageously be re-used in itself as a catalyst solution.

Further, since the catalyst system according to the present invention undergoes no deterioration of its catalytic activity even after repeated use, it is also possible to re-use the catalyst system after the repeated use by simply concentrating the catalyst system through removal of water in an amount corresponding to the amount of water formed during the reaction, which renders the process of the present invention industrially very advantageous from the standpoint of cost and pollution.

Further, the solvent mixture recovered after isolation of TMQ causes little or no change in the composition thereof even after the recovery and, therefore, can be re-used as the solvent for the reaction with supply of a small amount of a fresh solvent compensating for the amount of loss.

EXAMPLES

The examples of the present invention will now be described together with comparative examples for the purpose of specifically illustrating the effect of the present invention.

With respect to the following examples of the present invention, it is to be noted that only representative examples were described so that the present invention could more easily be understood. Therefore, it is needless to say that the present invention is not limited to these only.

The yield and residue as shown in Tables 1 to 5 were determined by the following methods.

1) Yield of TMQ and residue of TMP: in Comparative Examples 1 to 6 and Examples 1 to 26, the amount of TMQ contained in a crude product and the amount of the TMP remaining in the crude product were calculated through the quantitative determination by gas chromatography.

Since commercially available TMP having a purity of 97% as determined by gas chromatography was used as the starting material, a value obtained by dividing the found value by 0.97 was employed as the yield of TMQ.

2) Gas chromatography:

The quantitative determination by gas chromatography was conducted by making use of n-hexadecane as an internal standard under the following analytical conditions:

column: Fluoxylate-K 1%; Uniport HP 100/120; 2 mm$\phi \times 2.1$ m; glass column,
temperature: a column temperature of 105° C. and an injection temperature of 250° C.,
$N_2$ flow rate: 50 ml/min, detection method: FID.

COMPARATIVE EXAMPLES 1 to 5

A 200-ml four-necked flask was charged with 8.4 g (0.05 mol) of cupric chloride dihydrate, 8.4 g (0.2 mol) of lithium chloride, and 20 ml of distilled water, followed by dissolution, thereby preparing an aqueous catalyst solution.

Thereafter, 20 ml of a solvent listed in Table 1 was added to the aqueous catalyst solution, and an oxygen gas was bubbled at a flow rate of 200 ml/min into the resulting mixture at a position below the surface thereof while vigorously agitating the mixture at about 1000 rpm with a mechanical agitator and maintaining the temperature of the mixture at 60° C. through external heating. Then, a solution prepared by dissolving 6.8 g (0.05 mol) of TMP in 50 ml of the above-described solvent was added thereto by portions over a period of about 1 hr. After the completion of the addition, the reaction was continued for an additional 3 hr under the same conditions. After the completion of the reaction, the reaction mixture as poured into water. The resulting mixture was subjected to extraction twice with ethyl acetate in the case of Comparative Examples 1 to 3 and with the same solvent as the one for the reaction with respect to Comparative Examples 4 and 5. The extract was washed with water and then dried, followed by removal of the solvent, thereby obtaining a crude product.

The crude product thus obtained was applied to the quantitative determination by gas chromatography by making use of n-hexadecane as the internal standard to calculate the yield of TMQ and the reaction rate of TMP. The results are shown in Table 1.

EXAMPLE 1

A 200 ml four-necked flask was charged with 8.4 g (0.05 mol) of cupric chloride dihydrate, 8.4 g (0.2 mol) of lithium chloride, and 20 ml of distilled water, followed by dissolution, thereby preparing an aqueous catalyst solution.

Thereafter, 20 ml of a benzene/ethanol mixture (a volume ratio of 2 : 1) was added to the aqueous catalyst solution, and an oxygen gas was bubbled at a flow rate of 200 ml/min into the resulting mixture at a position below the surface thereof while vigorously agitating the mixture at about 900 rpm with a mechanical agitator and maintaining the temperature of the mixture at 60° C. through external heating.

Then, a solution prepared by dissolving 6.8 g (0.05 mol) of TMP in 50 ml of the above-described benzene/ethanol mixture was added thereto by portions over a period of about 1 hr. After the completion of the addition, the reaction was continued for additional 3 hr under the same conditions. After the completion of the reaction, the resulting organic phase was withdrawn from the organic phase and the water phase in a separated state. The water phase was subjected to extraction with a solvent mixture having the same composition as that of the reaction mixture. The extracts were combined, washed with water, and dried, followed by removal of the solvent.

With respect to the crude product thus obtained, the yield of TMQ and the reaction rate of TMP were calculated in the same manner as that of Comparative Examples 1 to 5. The results are shown in Table 1.

EXAMPLE 2

An aqueous catalyst solution was prepared according to the method described in Example 1. Thereafter, 70 ml of a benzene/ethanol mixture (a volume ratio of 2:1) and 6.8 g (0.05 mol) of TMP were dissolved in the aqueous catalyst solution, and an oxygen gas was bubbled at a flow rate of 200 ml/min into the solution at a position below the surface thereof while vigorously agitating the solution at about 900 rpm. The flask was gradually heated to keep the internal temperature of the flask at 60° C. The oxidation was continued for about 4 hr under this condition. Thereafter, the reaction mixture was subjected to post-treatment according to the method described in Example 1 to obtain a crude product The crude product was analyzed by gas chromatography in the same manner as that of Comparative Examples 1 to 5 to calculate the yield of TMQ and the reaction rate of TMP. The results are shown in Table 1.

TABLE 1

| | reaction solvent | yield of TMQ (%) | residue of TMP (%) |
|---|---|---|---|
| Comp. Ex. 1 | methanol | 47.9 | 0 |
| Comp. Ex. 2 | ethanol | 85.5 | 0 |
| Comp. Ex. 3 | n-propanol | 86.6 | 0 |
| Comp. Ex. 4 | benzene | 1.6 | 68.1 |
| Comp. Ex. 5 | toluene | 1.3 | 91.2 |
| Ex. 1 | benzene/ethanol | 94.0 | 0 |
| Ex. 2 | benzene/ethanol | 87.5 | 0 |

EXAMPLES 3 TO 12

Solvent mixtures which are different in the combination of the aromatic hydrocarbon with the lower aliphatic alcohol as well as in the composition ratio as shown in Table 2 were prepared. The reaction and the post-treatment were conducted according to the method described in Example 1 by making use of the above mixture as the solvent for the reaction and 8.4 g of each of cupric chloride dihydrate and lithium chloride and 6.8 g of TMP, thereby obtaining a crude product.

The crude product was analyzed by gas chromatography to calculate the yield of TMQ and the residue of TMP. The results are summarized in Table 2.

COMPARATIVE EXAMPLE 6

In order to examine a reaction solvent comprising benzene as the aromatic hydrocarbon and acetone as the hydrophilic solvent, a benzene/acetone mixture (a volume ratio of 2:1) were prepared, and the reaction and post-treatment were conducted according to the method described in Example 1, thereby obtaining crude product.

The gas chromatography of the crude product revealed that the yield of TMQ was lower than those of Examples 1 to 12 in which a lower alcohol was used and that, therefore, acetone was unsuitable as a hydrophilic solvent to be incorporated in the aromatic hydrocarbon. The results of the gas chromatography are shown in Table 2. The numeral "(1)" in the column of the examples of Table 2 refers to Example 1 which was described for easy comparison.

The same examination was conducted on ethyl acetate beside acetone. However, a large amount of by-products was formed, and the selectivity for TMQ was remarkably low. That is, no satisfactory results were obtained.

TABLE 2

| | reaction solvent | | | yield of TMQ (%) | residue of TMP (%) |
|---|---|---|---|---|---|
| | aromatic hydrocarbon | lower aliphatic alcohol | composition (volume ratio) | | |
| Ex. 3 | benzene | methanol | 3:2 | 89.0 | 0.5 |
| Ex. 4 | benzene | methanol | 2:1 | 86.0 | 0.9 |
| Ex. 5 | benzene | ethanol | 3:2 | 92.8 | 0 |
| Ex. (1) | benzene | ethanol | 2:1 | 94.0 | 1.1 |
| Ex. 6 | toluene | methanol | 2:1 | 82.7 | 0 |
| Ex. 7 | toluene | ethanol | 2:1 | 94.6 | 0 |
| Ex. 8 | toluene | ethanol | 4:1 | 91.7 | 0 |
| Ex. 9 | toluene | n-propanol | 2:1 | 94.1 | 0 |
| Ex. 10 | toluene | n-propanol | 3:1 | 93.8 | 0 |
| Ex. 11 | toluene | isopropanol | 2:1 | 91.6 | 0 |
| Ex. 12 | toluene | n-butanol | 2:1 | 92.9 | 0 |
| Comp. Ex. 6 | benzene | acetone | 2:1 | 35.0 | 0 |

EXAMPLES 13 to 19

Cupric chloride dihydrate and lithium chloride were added in various proportions as shown in Table 3 to 20 ml of water to prepare aqueous catalyst solutions. 20 ml of a toluene/n-propanol mixture (a volume ratio of 2 : 1) was added thereto. Thereafter, according to the method described in Example 1, 50 ml of a solution prepared by dissolving 50 mmol (6.8 g) of TMP in a toluene/n-propanol mixture (a volume ratio of 2 : 1) was added by portion under the same reaction conditions as those of Example 1 to conduct oxidation, followed by post-treatment. The results of the gas chromatography on the crude product are shown in Table 3. The numeral "(9)" in the column of the examples in Table 3 was described for the same purpose as that described above and refers to Example 9.

TABLE 3

| | TMP:CuCl$_2$.2H$_2$O:LiCl (mmol) | yield of TMQ (%) | residue of TMP (%) |
|---|---|---|---|
| Ex. 13 | 50:12.5:50 | 81.4 | 0.8 |
| Ex. 14 | 50:25:100 | 83.8 | 0.3 |
| Ex. 15 | 50:25:50 | 71.4 | 0 |
| Ex. 16 | 50:50:100 | 78.7 | 0 |
| Ex. 17 | 50:50:150 | 86.2 | 0 |
| Ex. (9) | 50:50:200 | 94.1 | 0 |
| Ex. 18 | 50:50:250 | 94.4 | 0 |
| Ex. 19 | 50:50:300 | 95.0 | 0 |

EXAMPLES 20 to 22

8.4 g (0.05 mol) of cupric chloride dihydrate, 8.4 g (0.2 mol) of lithium chloride, 20 ml of water, and a benzene/ethanol mixture (a volume ratio of 3 : 2) were mixed with each other to prepare a catalyst solution. According to the reaction conditions of Example 1, a solution prepared by dissolving 6.8 g (0.05 mol) of TMP in a benzene/ethanol mixture (a volume ratio of 3 : 2) was added to the catalyst solution by portions over a period of 2 hr while bubbling air instead of the oxygen gas at a flow rate of 200 ml/min into the catalyst solution at a position below the surface thereof. After the completion of the addition, the reaction was continued for an additional 3 hr.

After the completion of the reaction, the organic phase was withdrawn from the separated two phases. The water phase was once extracted with the same mixture as that described above. The extract was combined with the organic phase, washed with a small amount of water, dried, and then concentrated to obtained a crude product (Example 20).

The water phase was again returned to the reaction vessel. The reaction vessel was then charged with 6.8 g (0.05 mol) of fresh TMP in the same manner as that of Example 20 to conduct oxidation. This procedure was repeated three times in order to examine the capability of repetitive use of the catalyst solution in the air oxidation and the yield of TMQ. The results are shown in Table 4. "Ex. (5)" in Table 4 was described for the same purpose as that described above and refers to the above Example 5.

TABLE 4

| | frequency of repetition of use | kind of oxygen source gas | yield of TMQ (%) | residue of TMP (%) |
|---|---|---|---|---|
| Ex. (5) | | oxygen | 92.8 | 0 |
| Ex. 20 | 1 | air | 93.3 | 0 |
| Ex. 21 | 2 | air | 94.2 | 0 |
| Ex. 22 | 3 | air | 92.7 | 0 |

EXAMPLES 23 to 26

With the use of 6.8 g (0.05 mol) of TMP, the reaction and post-treatment were conducted in various combinations of reaction solvents as shown in Table 5 under conditions of varied reaction temperatures in the same manner as that of Example 1 to prepare a crude product.

In all the examples, TMP was added over a period of 1 hr, and the reaction was continued for an additional 3 hr after the completion of the addition. The crude product thus obtained was analyzed by gas chromatography to calculate the yield of TMQ and the residue of TMP. The results are shown in Table 5. The numerals "(7)" and "(11)" in the column of the examples in Table 5 were described for the same purpose as that described above and refer to the above Examples 7 and 11, respectively.

TABLE 5

| | reaction solvent (composition ratio by volume) | reaction temp. | yield of TMQ (%) | residue of TMP (%) |
|---|---|---|---|---|
| Ex. 23 | toluene/ethanol (2:1) | room temp. | 49.1 | 0.8 |
| Ex. 24 | toluene/ethanol (2:1) | 40° C. | 87.6 | 0.4 |
| Ex. (7) | toluene/ethanol (2:1) | 60° C. | 94.6 | 0 |
| Ex. 25 | toluene/ethanol (2:1) | 75° C. | 91.5 | 0 |
| Ex. (11) | toluene/isopropanol (2:1) | 60° C. | 91.6 | 0 |
| Ex. 26 | toluene/isopropanol (2:1) | 75° C. | 89.7 | 0 |

EXAMPLES 27 to 29

A 2-l reaction vessel was equipped with a mechanical stirrer having an excellent agitation efficiency, a thermometer, an air cooler, a thermometer, a bubbling pipe, and a dropping funnel. The reaction vessel was charged with 84 g of cupric chloride dihydrate, 84 g of lithium chloride, 200 ml of water, and 400 ml of a solvent mixture as shown in Table 6 to prepare a catalyst solution.

Then, a solution prepared by dissolving 68 g of TMP in 200 ml of the above-described solvent mixture was added by portions to the catalyst solution heated at 60° C. over a period of about 3 hr while vigorously agitating the catalyst solution at about 800 rpm and bubbling an oxygen gas (a flow rate of 200 ml/min) into the catalyst solution at a position below the surface thereof.

After the completion of the addition, the reaction was continued for an additional 1 hr under the same conditions, thereby completing oxidation.

After the completion of the reaction, the resulting organic phase was withdrawn from separated two phases. The water phase was extracted with a solvent mixture having the same composition as that of the reaction solvent. The extract was combined with the organic phase and washed with a small amount of water, followed by removal of the solvent under a reduced pressure by means of an aspirator. The orange-colored oleaginous residue thus obtained was subjected to vacuum distillation or steam distillation, thereby obtaining an orange-colored oleaginous substance (which crystallizes when being cooled). The amount, yield, purity, and boiling point of the product with respect to each example are shown in Table 6.

TABLE 6

|  | reaction solvent (mixing ratio by volume) | yield[1] of TMQ (g) | purity[2] (%) | yield[3] of TMQ (%) | boiling point (°C./ mmHg) |
|---|---|---|---|---|---|
| Ex. 27 | toluene/n-propanol (2:1) | 70.3 | 97.6 | 94.3 | 90–91/1.0 |
| Ex. 28 | toluene/ethanol (2:1) | 73.8 | 91.8 | 93.1 | steam distillation |
| Ex. 29 | toluene/isopropanol-denatured ethanol (2:1) | 68.0 | 97.8 | 91.4 | 89–90/0.8 |

Note:
[1] Weight of TMQ obtained by distillation.
[2] Gas chromatography was conducted in the same manner as that of Tables 1 to 5 by making use of n-hexadecane as the internal standard to determine the amount of TMQ contained in the product purified by distillation, followed by calculation of the purity of TMQ (%).
[3] $\frac{\text{amount of TMQ (g)} \times \text{purity (\%)}}{\left(\begin{array}{c}\text{calculated}\\\text{amount of TMQ}\end{array}\right) 76\text{ g} \times 0.97 \left(\begin{array}{c}\text{purity}\\\text{of TMP}\end{array}\right)}$ (%)

We claim:

1. A process for preparing a 2,3,5-trimethylbenzoquinone which comprises:
   agitating (a) an organic phase of 2,3,6-trimethylphenol and a solvent mixture of an aromatic hydrocarbon and a lower aliphatic alcohol having 1 to 4 carbon atoms and (b) an aqueous phase comprising a catalyst of cupric chloride and lithium chloride and water, to form a fine dispersion;
   bringing said fine dispersion into contact with molecular oxygen or a molecular oxygen-containing gas to effect the oxidation of said 2,3,6-trimethylphenol to 2,3,5-trimethyl-benzoquinone in said organic phase; and
   separating said organic phase from said aqueous phase.

2. The process as claimed in claim 1, in which said solvent mixture comprises said aromatic hydrocarbon and said lower aliphatic alcohol at a volume ratio of 1 : 0.2 to 1.

3. The process as claimed in claim 1, in which said aromatic hydrocarbon is selected from the group consisting of benzene, toluene, xylene and chlorobenzene.

4. The process as claimed in claim 1, in which said alcohol is selected from the group consisting of methanol, ethanol, n-propanol, isopropanol, n-butanol, 2-butanol and tertbutanol.

5. The process as claimed in claim 1 or 2, in which said solvent mixture comprises toluene or benzene and ethanol or n-propanol.

6. The process as claimed in claim 1 or 2, in which said solvent mixture comprises benzene and ethanol.

7. The process as claimed in claim 1 or 2, in which said solvent mixture comprises toluene and n-propanol.

8. A process as claimed in claim 1, which further comprises the step of recovering said solvents by distillation of said organic phase and separately said aqueous phase for re-use thereof.

* * * * *